United States Patent
Greiner et al.

(10) Patent No.: US 10,687,763 B2
(45) Date of Patent: Jun. 23, 2020

(54) SPO2 TONE MODULATION WITH AUDIBLE LOWER CLAMP VALUE

(71) Applicant: KONINKLIJKE PHILIPS N.V., Eindhoven (NL)

(72) Inventors: Harald Greiner, Nufringen (DE); Wilhelm Meier, Herrenberg (DE); Frank Enslin, Deckenfronn (DE); Rolf Neumann, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 842 days.

(21) Appl. No.: 14/895,505

(22) PCT Filed: Jun. 13, 2014

(86) PCT No.: PCT/IB2014/062200
§ 371 (c)(1),
(2) Date: Dec. 3, 2015

(87) PCT Pub. No.: WO2014/207597
PCT Pub. Date: Dec. 31, 2014

(65) Prior Publication Data
US 2016/0106379 A1  Apr. 21, 2016

Related U.S. Application Data

(60) Provisional application No. 61/838,373, filed on Jun. 24, 2013.

(51) Int. Cl.
*A61B 5/00* (2006.01)
*A61B 5/145* (2006.01)

(52) U.S. Cl.
CPC ........ *A61B 5/7415* (2013.01); *A61B 5/14542* (2013.01)

(58) Field of Classification Search
CPC .......................... A61B 5/7415; A61B 5/14542
See application file for complete search history.

(56) References Cited

U.S. PATENT DOCUMENTS 5,730,140 A * 3/1998 Fitch .................... A61B 5/0205
   600/514
5,796,854 A * 8/1998 Markow ............... G06F 1/1616
   381/385

(Continued)

FOREIGN PATENT DOCUMENTS

| JP | S59160446 | 9/1984 |
| JP | H11244246 | 9/1999 |
| WO | 2012/1300274 | 10/2012 |

OTHER PUBLICATIONS

Yost, "Pitch Perception", Attention, Perception, & Psychophysics, vol. 71(8), p. 1701-1715, 2009 (Year: 2009).*

*Primary Examiner* — Eric F Winakur
*Assistant Examiner* — Abid A Mustansir

(57) ABSTRACT

A patient monitor device includes one or more sensors which measure physiological parameters of a patient, a controller which controls an audio source to generate an audible tone and adjust the pitch or frequency of the audible tone to indicate the measured physiological parameter according to a mapping scheme, the audio source which generates the audible tone, and an audio output device which outputs the audible tone. The mapping scheme clamping a frequency of the audible tone after reaching a predetermined threshold.

12 Claims, 2 Drawing Sheets

(56) References Cited

U.S. PATENT DOCUMENTS

| | | | |
|---|---|---|---|
| 6,449,501 B1 | 9/2002 | Reuss | |
| 6,542,764 B1* | 4/2003 | Al-Ali | A61B 5/02416 |
| | | | 600/323 |
| 6,947,780 B2 | 9/2005 | Scharf | |
| 7,149,570 B2 | 12/2006 | Ellscheid et al. | |
| 9,702,969 B2 | 7/2017 | Hope Simpson | |
| 2004/0193026 A1* | 9/2004 | Scharf | A61B 5/00 |
| | | | 600/323 |
| 2004/0243016 A1 | 12/2004 | Sanderson et al. | |
| 2005/0046575 A1* | 3/2005 | Cooper | G08B 3/10 |
| | | | 340/573.1 |
| 2005/0240396 A1* | 10/2005 | Childs | G10H 1/0025 |
| | | | 704/207 |
| 2007/0230712 A1 | 10/2007 | Belt | |
| 2007/0293745 A1 | 12/2007 | McCutcheon et al. | |
| 2010/0049061 A1 | 2/2010 | Wilson | |
| 2011/0080294 A1* | 4/2011 | Tanishima | A61B 5/1455 |
| | | | 340/573.1 |
| 2011/0249843 A1* | 10/2011 | Holmberg | H04R 25/353 |
| | | | 381/316 |
| 2013/0044896 A1* | 2/2013 | Ekstrand | G10H 1/16 |
| | | | 381/98 |

\* cited by examiner

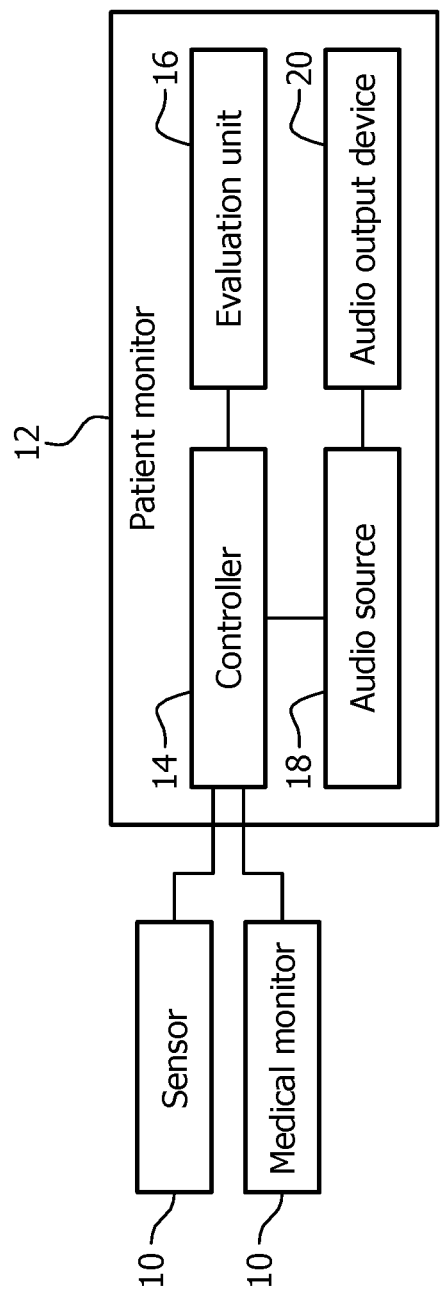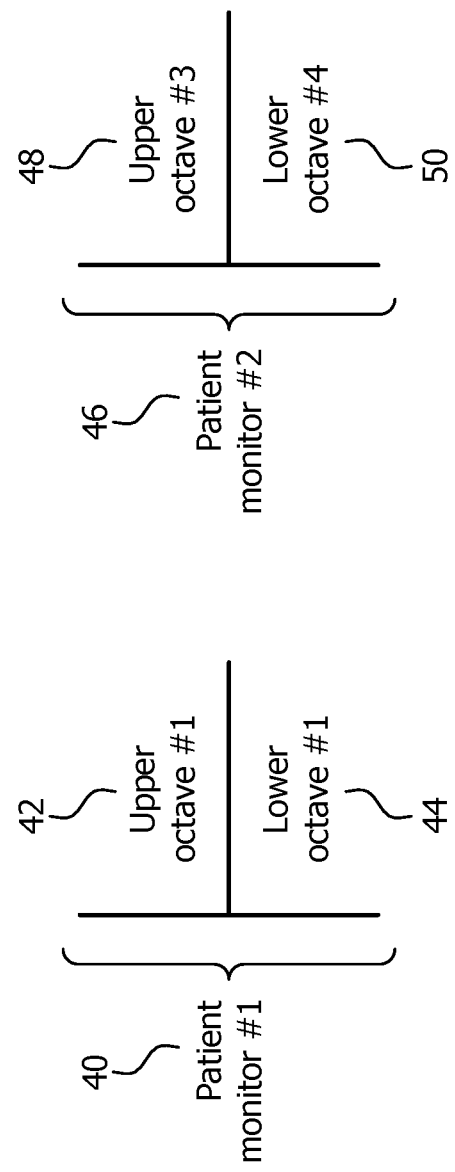

SPO2 TONE MODULATION WITH AUDIBLE LOWER CLAMP VALUE

CROSS REFERENCE TO RELATED APPLICATIONS

This application is a national filing of PCT application Serial No. PCT/IB2014/062200, filed Jun. 13, 2014, published as WO 2014/207597 on Dec. 31, 2014, which claims the benefit of U.S. Provisional Application No. 61/838,373 filed Jun. 24, 2013, all of which are incorporated herein by reference.

The present application relates generally to patient monitoring. It finds particular application in conjunction with SpO2 tone modulation with an audible lower clamp value and will be described with particular reference thereto. However, it is to be understood that it also finds application in other usage scenarios and is not necessarily limited to the aforementioned application.

Pulse oximetry typically involves measurement of the saturated percentage of oxygen in the blood as well as the rate of blood pulsations corresponding to each heartbeat of a patient. Traditionally, pulse oximeter monitors produce tonal signals which have a pitch proportional to the ratio of oxygen saturation and a sequential repetition proportional to the pulse. For example, typical pulse oximeters generate a quick response tone with a fixed frequency for every heartbeat of a patient. Further, these pulse oximeters modulate this tone by mapping the full range of SpO2 values (100% to 0%) to a specific range of different audible frequencies for that tone. This mapping is usually done utilizing a linear relation between the SpO2 values and the frequency of that tone. For example, linear relation mapping produces a tone at a frequency of 662 Hz for a 100% SpO2 value and a tone at a frequency of 163 Hz for a 0% SpO2 value. Another version of this mapping utilizes a logarithmic relationship which matches much better with the human perception of a sequence of tone pitches. A logarithmic relation mapping also produces a tone at a frequency of 662 Hz for a 100% SpO2 value, however, for each 24% drop in SpO2, the frequency of the tone is cut in half. For example, a tone at a frequency of 331 Hz will be produced for a 76% SpO2 value, a tone at a frequency of 165.5 Hz will be produced for a 52% SpO2 value, a tone at a frequency of 82.75 Hz will be produced for a 28% SpO2 value, and a tone at a frequency of 41.37 Hz will be produced for a 4% SpO2 value.

However, in humans, the audible range of frequencies usually ranges from 20 to 20,000 Hz. For both linear and logarithmic relation mapping, the frequency for low SpO2 values are quite low thus making it difficult if not impossible to hear. Typically, the upper frequency for a 100% SpO2 value is chosen to be well supported by the audio system. Providing a mapping such that the frequency of a low SpO2 value is supported by the audio system and can be heard and discerned by the user is very difficult. Further, with a family of monitors with different audio outputs and different limitations of their frequency bands, the produced tones are very ambiguous and inconsistent thus making it difficult to recognize a particular monitor producing a certain tone.

The present application provides new and improved methods and system which overcome the above-referenced problems and others.

In accordance with one aspect, a patient monitoring device is provided. The device includes one or more sensors which measure physiological parameters of a patient, a controller which controls an audio source to generate an audible tone and adjust the pitch of the audible tone to indicate the measured physiological parameter according to a mapping scheme, the audio source which generates the audio tone, and an audio output device which outputs the audible tone. The mapping scheme clamping a frequency of the audible tone after reaching a predetermined threshold.

In accordance with another aspect, a method for tone modulation with an audible lower clamp value is provided. The method including measuring physiological parameters of a patient with one or more sensors and generating an audible tone and adjusting the pitch of the audible tone to indicate the measured physiological parameter according to a mapping scheme. The mapping scheme clamping a frequency of the audible tone after reaching a predetermined threshold.

In accordance with another aspect, a method is provided. The method including outputting a first audible tone from a first patient monitor with a first audio output device, outputting a second audible tone from a second patient monitor with a second audio output device, the second audio output device having a different audio characteristics than the first audio output device, and transposing the first and second audible tones such that the audible tone being produced matches the audio characteristics of the audio output device.

One advantage resides in providing a mapping scheme which enables low SpO2 values to be heard and easily discerned by a user.

Another advantage resides in defining a lower range limit for SpO2 tone modulation.

Another advantage resides in transposing tones to address different frequency characteristics of various audio output devices.

Another advantage resides in improved patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 illustrates a block diagram of a patient monitoring device according to aspects of the present application.

FIG. 2 illustrates a block diagram of multiple patient monitoring devices according to aspects of the present application.

Figure 3:
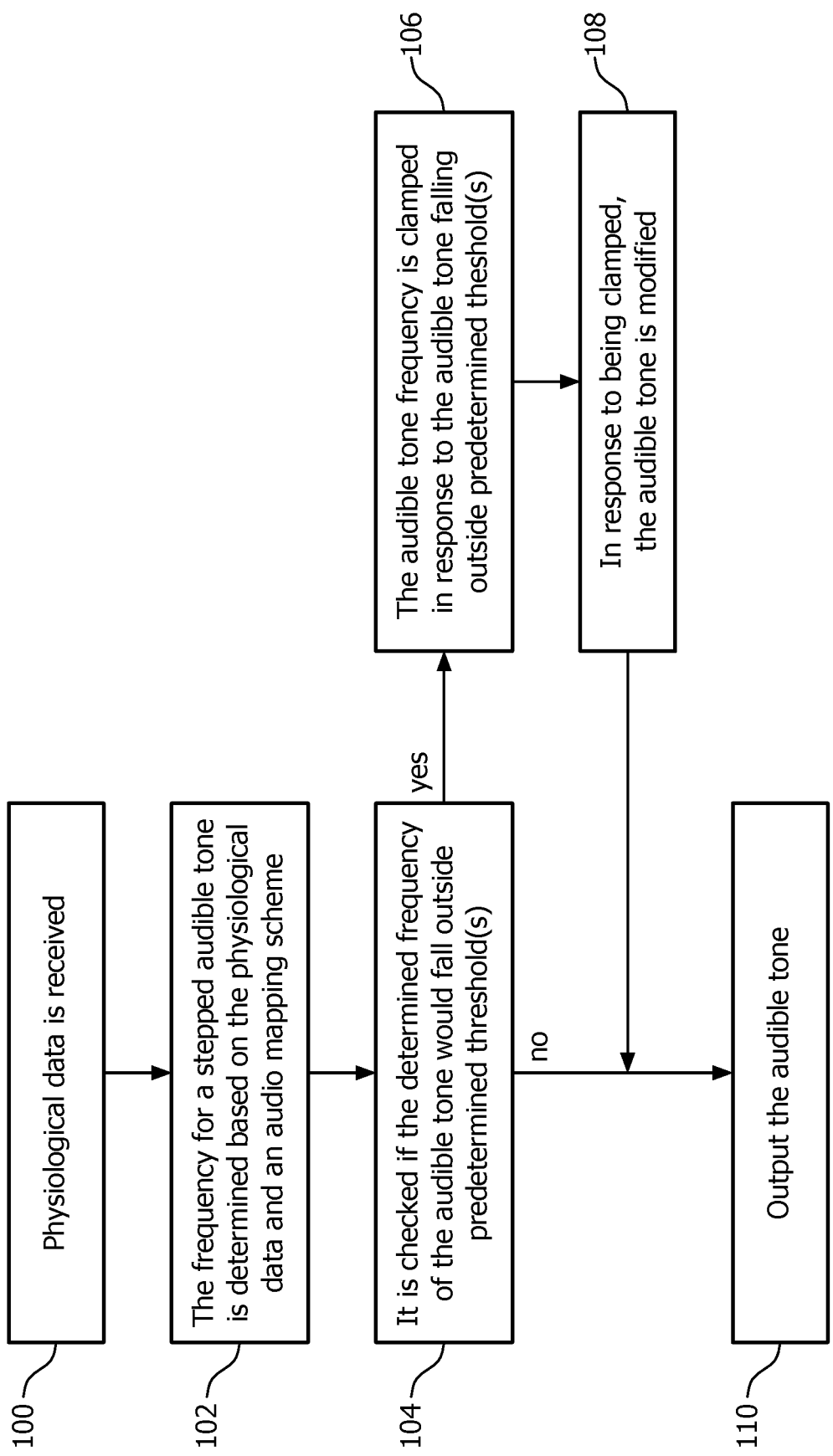
FIG. 3 illustrates a flowchart diagram of a method tone modulation with an audible lower clamp value to aspects of the present application.

The present application is directed to Sp02 tone modulation with an audible lower clamp value. One aspect of the present application is directed to limiting the value for the audible frequency to a reasonable clinical value (e.g. 52%=165.5 Hz for a logarithmic relationship). The user is aware of this audible clamp by modifying other aspects of the tone being output. For example, a double pulse can be provided with a two times 30 milliseconds duration with a space of 20 milliseconds instead of a tone with a 80 milliseconds duration. Another method may use a specific audio tone signal or combine two different audio tone signals such as combining the usual tone for Sp02 clamp with a specific "clamp" tone. Such a scheme avoid tones with lower frequencies representing very low values which may not be heard as the volume of the audible output device may decline in those low ranges. Clamping at a reasonable low frequency and changing the pattern to indicate dangerous SpO2 values is much more clinically appropriate. Further, if sounds are used in a family of devices with different audio output device which have different limitations in their frequency band, those sounds are still almost immediately recognizable by the user. Another aspect of the present application is directed to transposing known sounds that were design for classic output devices, such as speakers to, be used for other smaller audio output device, such as piezo audio elements. For example, transposing an audio tone up three octaves for a piezo audio element may provide an audio signal which can easily be heard or discerned by the user.

With reference to FIG. 1, a patient (not shown) is monitored by various medical monitoring devices or sensors 10 that measure physiological parameters of the patient and generate physiological data indicative thereof. These medical monitoring devices 10 may include a blood oxygenation ($SpO_2$), an electrocardiographic (ECG) instrument with ECG electrodes, a medical monitor, which may for example be configured to blood oxygenation ($SpO_2$), pulse, or one or more other physiological parameters. Other medical monitoring devices 10 can be associated with a patient, and not all of the above-mentioned medical monitoring devices 10 have to be associated with a patient at any given time. It should be appreciated that while only two medical monitoring devices 10 are illustrated, one or more medical monitoring devices are contemplated. As used herein, medical monitoring devices signifies data sources indicating patient health, or the like. Electronics for receiving signals from the medical monitoring device and for optionally performing signal processing on such signals are embodied in the illustrated embodiment as a multi-functional patient monitor device 12. The patient monitor device 12, for example, may be a monitor that travels with the patient, such as the transmitter of an ambulatory patient worn monitoring system, or the like.

The medical monitoring devices 10 report the measured or other physiological data to the patient monitor device 12. The patient monitor device 12 serves as a gathering point for the physiological data measured by the medical monitoring devices, and provides temporary storage for the data. The collected physiological data is concurrently transmitted to a controller 14 in the patient monitor device 12. A physiological evaluation unit 16 or computer program in the patient monitor device evaluates the physiological data collected from the patient and determines whether the patient's condition warrants notifying an appropriate medical responder by generating an alarm signal. For example, the patient monitor device 12 checks whether each measured parameter is approaching threshold values, whether a trend of any parameter is approaching a threshold, whether any parameter lacks stability or fluctuates too much, combinations of parameters are approaching a threshold, and other indicators that a patient needs more or less medical monitoring or assistance. The thresholds include values exceeding a limit based on time, severity, escalation, or the like.

The controller 14 in the patient monitor device 12 also controls an audio source 18 to produce an audible tone which output of an audio output device 20 based on the physiological data. The audio output device includes an electric acoustic transducer, a classic speaker, piezo elements, and the like. For example, the controller 14 controls the audio source 18 to output a short audible tone for each characteristic point in a cardiac cycle. The controller 14 also controls the audio source 18 adjust the pitch of the short audible tone to indicate SpO2 concentration. Specifically, the physiological evaluation unit 16 evaluates the collected physiological data to determine a measurement of the saturation percentage of oxygen in the blood as well as the rate of blood pulsation corresponding to each heartbeat of a patient. The controller 14 then controls the audio source 18 to output an audible tone based on the oxygen saturation and a sequential repetition proportional to the pulse. As stated above, utilizing typical linear and logarithmic relation mapping schemes to indicate SpO2 concentration and pulse result in numerous problems for the user. The present application addresses these problems by providing an audio mapping scheme which enables low SpO2 values to be heard and easily discerned by a user and defines a lower range limit for SpO2 tone modulation.

Specifically, the controller 14 controls the audio source 18 to output audible tones based on a musical scale, which is non-linear. That is, each octave doubles the frequency. For example, upper C is twice the frequency of middle C. The mapping scheme utilized by the controller 14 step the frequency in the audible tone in full-tone or half-tone increments which are easier for the human ear to distinguish and recognize. For example, the mapping scheme produces a tone at a frequency of 5296 Hz for a 100% SpO2 value, however, for each 24% drop in SpO2, the frequency of the tone is cut in half. In other words, for each 1% change in the blood oxygen concentration the frequency is changed by a half-tone. For example, a tone at a frequency of 2648 Hz will be produced for a 76% SpO2 value, a tone at a frequency of 1324 Hz will be produced for a 52% SpO2 value. The blood oxygen concentrations are also based on a musical scale such that the 100% SpO2 value is upper C and the 52% SpO2 value is lower C. However, due to the challenging hearing or discerning below this frequency range, the frequency of the audible tone is clamped after two octaves or a predetermined threshold. Specifically, after the frequency of the audible tone reaches a predetermined threshold, the frequency would no longer step down and remaining at the predetermined clamp frequency. For example, the frequency of the audible tone is clamped after the 1324 Hz for a 52% SpO2 value, or a quarter of the 5296 Hz for a 100% SpO2 value. Once the lower clamp value is reached, the frequency would no longer step down. Rather, the lowest frequency would merely indicate that the blood oxygen is critically low and needs immediate attention. In another embodiment, once the lower clamp value is reached, other aspects of the audible tone are modified. For example, for saturation values below the lower clamp value, a tone at a frequency of 1324 Hz is produced with a double pulse in order to differentiate it from the 52% SpO2 concentration. In another example, after the lower clamp value, a specific "clamp" tone or a combination of the usual tone and the specific "clamp" tone are produced. It is contemplated that this mapping scheme is utilized to represent physiological parameters other than SpO2 concentration. It is also contemplated that the threshold and clamp value can also be at the upper end of a range. It is further contemplated that the mapping scheme is also used to indicate various behaviors of the physiological parameters including the physiological parameters approaching threshold values, whether a trend of any parameter is approaching a threshold, whether any parameter lacks stability or fluxuates too much, combinations of parameters are approaching a threshold, and other indicators that a patient needs more or less medical monitoring or assistance.

In another embodiment, the controller 14 transposes the audible tone based on the type of audio output device 20. For example, various types of audio output devices 20 have different audio characteristics and tonal frequency limitations. For instance, a classic output speaker device such as a speaker (662 Hz) has a much lower optimal frequency range than a smaller audio output device such as a piezo element (5296 Hz). As such, the controller 14 transposes the audible tone being produced to best match the audio characteristics of the audio output device 20 being used. For example, if a classic speaker is being used as the audio output device 20, the controller 14 will transpose the audible tone to being around the 662 Hz range, whereas if a piezo element is being used as the audio output device 20, the controller 14 will transpose the audible tone to be around the 5296 Hz range.

In another embodiment, if multiple patient monitor devices 12 are being used with different audio output devices 20 and those patient monitor devices 12 utilize the same mapping scheme, the controller 14 transposes the audible tone, such that audible tone will operate in different octaves. As shown in FIG. 2, utilizing the above clamp mapping scheme, a first patient monitor device 40 will operate in upper octave #1 42 and lower octave #2 44 and a second patient monitor device 46 will operate in upper octave #48 and lower octave #4 50. It is important to note that each of the octaves is different from one another such that the user can differentiate between patient monitor devices. Thus, for a family of patient monitor devices with different audio output devices all the audible tones are unambiguous but still consistent.

With reference to FIG. 3, a method for providing tone modulation with an audible lower clamp value is illustrated. In a step 100, physiological data is received. The frequency for a stepped audible tone is determined based on the physiological data and an audio mapping scheme in a step 102. In a step 104, it is checked if the determined frequency of the audible tone would fall predetermined threshold(s). In a step 106, the audible tone is clamped in response to the audible tone falling outside predetermined threshold(s). In response to being clamped, the audible tone is modified in a step 108. In step 110 the audible tone is output.

In another embodiment the mapping already includes the clamping in a way that physiological data outside the predetermined threshold(s) is directly mapped to the clamped audible tone.

One having ordinary skill in the art will appreciate in view of the teachings provided herein, features, elements, components, etc. described in the present disclosure/specification and/or depicted in the appended Figures and/or any other Appendixes, may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read-only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for systems, methods and others, for example (which embodiments are intended to be illustrative and not limiting), it is noted that modifications and variations can be made by persons skilled in the art in light of the teachings provided herein, including the Figures and Appendixes. It is therefore to be understood that changes can be made in/to the preferred and exemplary embodiments of the present application which are within the scope of the embodiments described herein. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A patient monitoring device, the device comprising:
   one or more sensors configured to measure a blood oxygen concentration of a patient;
   an audio source;
   a controller configured to control the audio source to generate an audible tone and adjust a frequency of the audible tone to indicate the measured blood oxygen concentration according to a non-linear mapping scheme that corresponds to an octave-based musical scale in which an octave is double a frequency of the tone;

an audio output device which outputs the audible tone;

wherein the mapping scheme clamps the frequency of the audible tone after reaching a predetermined threshold; and wherein the controller is further configured to, for each one percent change in the blood oxygen concentration, step the frequency of the audible tone in accordance with the non-linear mapping scheme by one half tone or one full tone of the octave-based musical scale.

2. The device according to claim 1, wherein the audible tone includes an audible tone for each characteristic point in a cardiac cycle.

3. The device according to claim 1, wherein the predetermined threshold is two octaves below a peak frequency.

4. The device according to claim 1, wherein the controller modifies the audible tone after reaching the predetermined threshold.

5. The device according to claim 1, wherein the controller transposes the audible tone based on a type of the audio output device.

6. The device according to claim 1, wherein the controller is further configured to:

transpose the audible tone based on a type of the audio output device.

7. A system comprising:

a first patient monitoring device comprising a patient monitoring device according to claim 1; and a second patient monitoring device comprising a patient monitoring device according to claim 1;

wherein the controller of the first patient monitoring device is configured to transpose the audible tone of the first patent monitoring device to operate in a different octave than the audible tone of the second patient monitoring device.

8. A method for tone modulation with an audible lower clamp value, the method comprising:

measuring a blood oxygen concentration of a patient with one or more sensors;

generating an audible tone and adjusting a frequency of the audible tone to indicate the measured blood oxygen concentration according to a non-linear mapping scheme that corresponds to an octave-based musical scale in which an octave is double a frequency of the tone, wherein the non-linear mapping scheme clamps the frequency of the audible tone after reaching a predetermined threshold; and stepping the frequency of the audible tone in full-tone or half-tone increments based on the blood oxygen concentration;

wherein for each one percent change in the blood oxygen concentration the frequency is changed by one half-tone or one full-tone of the octave-based musical scale.

9. The method according to claim 8, wherein the audible tone includes an audible tone for each characteristic point in a cardiac cycle.

10. The method according to claim 8, wherein the predetermined threshold is two octaves below a peak frequency.

11. The method according to claim 8, further including:

modifying the audible tone after reaching the predetermined threshold.

12. The method according to claim 8, further including:

transposing the audible tone based on a type of audio output device.

* * * * *